(12) United States Patent
Cheim et al.

(10) Patent No.: US 9,383,315 B2
(45) Date of Patent: Jul. 5, 2016

(54) SENSOR STRUCTURE FOR ONLINE MONITORING OF FURANS IN POWER TRANSFORMERS

(71) Applicant: ABB Technology AG, Zurich (CH)

(72) Inventors: Luiz V. Cheim, St. Charles, MO (US); Oleg Kouzmine, Leipzig (DE); Robert Wueest, Zurich (CH)

(73) Assignee: ABB Technology AG, Zurich (CH)

( * ) Notice: Subject to any disclaimer, the term of this patent is extended or adjusted under 35 U.S.C. 154(b) by 182 days.

(21) Appl. No.: 14/351,890

(22) PCT Filed: Oct. 10, 2012

(86) PCT No.: PCT/US2012/059417
§ 371 (c)(1),
(2) Date: Apr. 15, 2014

(87) PCT Pub. No.: WO2013/059032
PCT Pub. Date: Apr. 25, 2013

(65) Prior Publication Data
US 2014/0291536 A1    Oct. 2, 2014

Related U.S. Application Data

(60) Provisional application No. 61/549,793, filed on Oct. 21, 2011.

(51) Int. Cl.
*G01N 21/59* (2006.01)
*G01N 21/33* (2006.01)

(52) U.S. Cl.
CPC ............... *G01N 21/59* (2013.01); *G01N 21/33* (2013.01); *G01N 2201/062* (2013.01); *G01N 2201/084* (2013.01)

(58) Field of Classification Search
CPC . G01N 21/59; G01N 21/33; G01N 2201/062; G01N 2201/084
See application file for complete search history.

(56) References Cited

U.S. PATENT DOCUMENTS

| 3,308,712 A * | 3/1967 | Kay ...................... G01J 3/1256 356/410 |
| 3,925,220 A | 12/1975 | Mills |
| 6,573,493 B1 * | 6/2003 | Futami .................. H01J 49/162 250/282 |

FOREIGN PATENT DOCUMENTS

| CA | 2054616 A1 | 5/1993 |
| EP | 0816830 A2 | 1/1998 |
| JP | EP 0816830 A2 * | 1/1998 ............. G01N 21/31 |

OTHER PUBLICATIONS

Abu-Saida, A. "Correlation of Furan Concentration and Spectral Response of Transmformer Oil-Using Expert Systems," IET Sci. Meas. and Technol., 2011, 5 (5), pp. 183-188.*
International Search Report & Written Opinion in PCT/US12/59417 dated Dec. 19, 2012.

* cited by examiner

*Primary Examiner* — Casey Bryant
(74) *Attorney, Agent, or Firm* — Manelli Selter PLLC; Edward J. Stemberger

(57) ABSTRACT

Sensor structure (16) is provided for online monitoring of levels of Furans in oil of a transformer tank. The sensor structure includes a UV light source (26), a filter (30) permitting only UV light of a certain wavelength range to pass, a window (32) permitting the filtered UV light to passes therethrough and a UV light detector (36) to receive UV light that passes through the window. When the sensor structure is mounted to the transformer tank that is online so that the window is exposed to oil, and Furans in the oil are being monitored, the Furans will absorb UV light, creating a difference in UV light received by the light detector when compared to the UV light received by the light detector when the monitored oil has no Furans therein. The output signal of the light detector is substantially proportional to a total of Furans in the monitored oil.

20 Claims, 2 Drawing Sheets

SENSOR STRUCTURE FOR ONLINE MONITORING OF FURANS IN POWER TRANSFORMERS

FIELD OF THE INVENTION

The invention relates to power transformers and, more particularly, to an online sensor structure for online monitoring the level of Furans in transformer oil.

BACKGROUND OF THE INVENTION

Worldwide utilities generate databases of Furans, which is a group of chemical compounds found dissolved in transformer oil that come only from cellulose degradation. Most transformer experts require the information regarding the levels of Furans in the oil before making a decision with respect to transformer failure, end of life, etc. These compounds were discovered in the early 1980's and since then, have created a great interest at CIGRE, IEEE and major utilities around the globe.

Furans are normally detected after an offline oil sample is taken from the transformer and sent to a chemical lab for processing in a device called a high performance liquid chromatography (HPLC). The oil sample is typically taken when samples are also taken for gas in oil analysis or for standard oil tests.

Thus, there is a need to provide an online sensor for monitoring Furans in a transformer.

SUMMARY OF THE INVENTION

An object of the invention is to fulfill the need referred to above. In accordance with the principles of the present invention, this objective is achieved by providing sensor structure for online monitoring of levels of Furans in oil of a transformer tank. The sensor structure includes an ultraviolet (UV) light source, a filter permitting only UV light of a certain wavelength range to pass the filter, a transparent window constructed and arranged so that the filtered UV light passes there-through, and a UV light detector constructed and arranged to receive UV light that passes through the window. When the sensor structure is mounted with respect to a transformer tank that is online so that the window is exposed to oil, and Furans in the oil are being monitored, the Furans will absorb UV light, thus creating a difference in UV light received by the light detector when compared to the UV light received by the light detector when the monitored oil has no Furans therein. The light detector is constructed and arranged to provide an output signal that is substantially proportional to a total of Furans in the monitored oil.

In accordance with another aspect of the invention, a method is provided for online monitoring of levels of Furans in oil of a transformer tank. The method provides a source of UV light. The UV light is filtered to a certain wavelength range. A transparent window is exposed to oil of the transformer tank. The filtered UV light is passed through the window while the transformer is online. The UV light that passes through the window is received by a light detector, with an output signal of the light detector being substantially proportional to a total of Furans in the oil being monitored.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings wherein like numbers indicate like parts, in which.

DETAILED DESCRIPTION OF THE EXEMPLARY EMBODIMENTS

Figure 1:
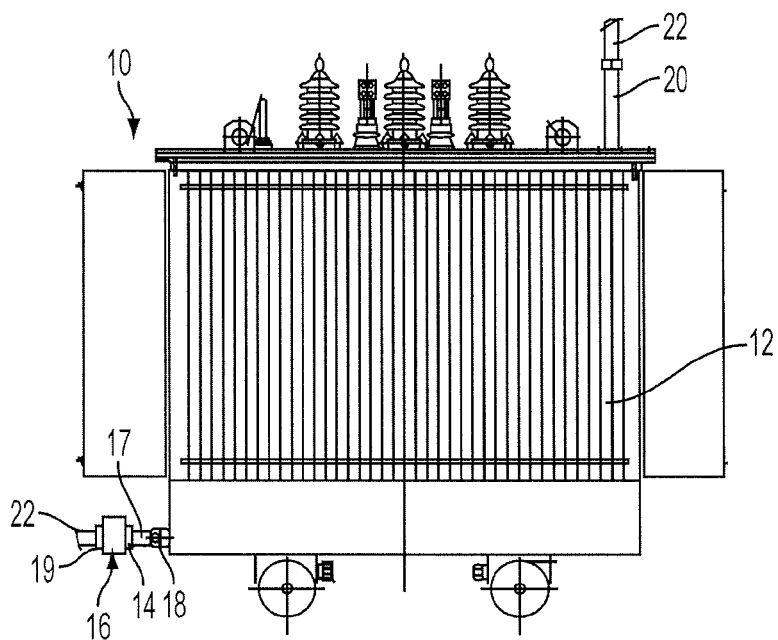
FIG. 1 is a schematic view of a transformer having a Furan sensor structure coupled thereto, in accordance with the present invention.

With reference to FIG. 1, a transformer, generally indicated at 10, includes a transformer tank 12 that is filled with insulating oil to insulate components therein, such as a tap changer (not shown). An inlet 14 of a Furan sensor structure, generally indicated at 16, is coupled to the drain valve 18 of the tank 12 via an oil duct 17. An outlet 19 of the sensor structure 16 communicates with a fill port 20 at the top of the tank 12 via a second oil duct 22. It is noted that that in FIG. 1, only portions of the second oil duct 22 are shown. Thus, transformer oil from the tank 12 exits the drain valve, passes through the sensor structure 16, and then is directed back into the tank via port 20.

Figure 2:
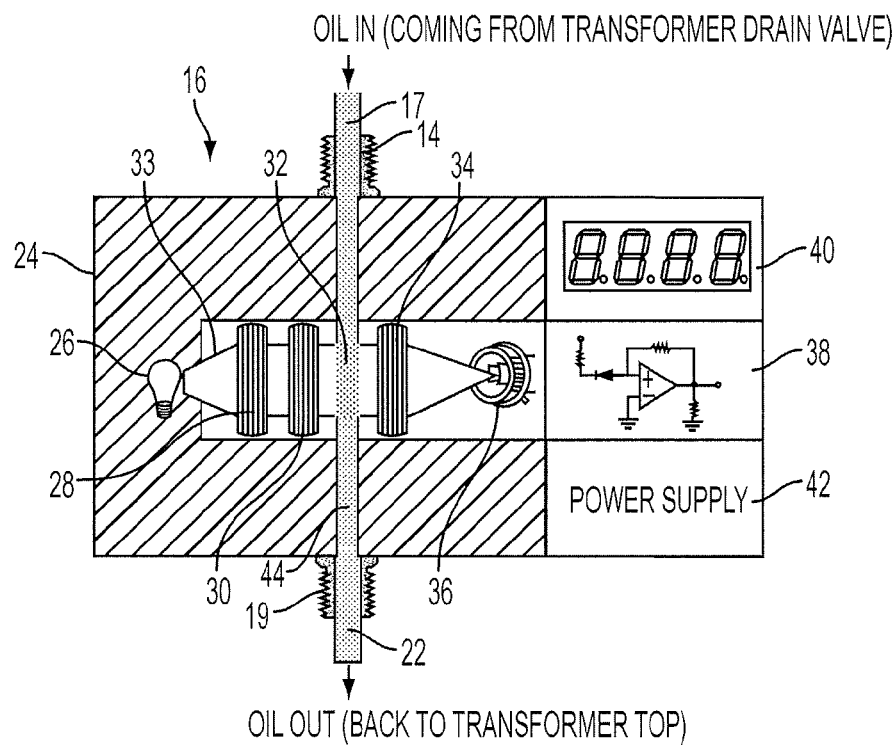
FIG. 2 is an enlarged view of the sensor structure of FIG. 1.

With reference FIG. 2, the non-invasive sensor structure 16 includes a single sensor housing 24 that contains an ultraviolet (UV) light source 26, a collimating lens 28, a low band (e.g., 225-330 nm) filter 30, a transparent optical (e.g., glass) window 32 allowing the UV light to pass there-through and disposed between the inlet 14 and the outlet 19, a condensing lens 34 and a UV photodiode or light detector 36. An operational amplifier (OPAMP) 38 amplifies the output of the light detector 36. The output of the OPAMP 38 is an electrical signal substantially proportional to the total Furans, mainly the most common element 2FAL=2 Furfuraldehyde. There is a need to calibrate this output to the actual amounts of Furan in the oil since the output may vary with the optical path, electronics, etc. The output of the OPAMP 38 is displayed on a display 40. The display 40 can be analog or digital or even an audible signal can indicate an alarm condition. A universal power supply 42, preferably disposed within the housing 24, provides power to the sensor structure 16. The OPAMP 38, display 40, and the power supply 42 are also preferably disposed in the housing 24.

In accordance with the embodiment of FIG. 2, in order to monitor the level of Furans in the oil in the tank 12, oil 44 from the tank 12 passes through the drain valve 18 through the inlet 14 of the sensor structure 16 and past the glass window 32. The UV light source emits UV light 33 that passes through the lens 28 and filter 30 and glass window 32. Furans are strong absorbers of UV-VIS light, particularly in the 225-330 nm range. If Furans are within the oil, the Furans will absorb UV light, thus creating a difference in UV light received by the light detector 36 when compared to the UV light received by the light detector 36 when the oil has no Furans therein. As noted above, the output of the OPAMP 38 is substantially proportional to the total Furans in the oil being monitored and the output of the OPAMP 38 is displayed on a digital display 40. The oil 44 then passes through outlet 19 and is returned to the tank via port 20.

Figure 3:
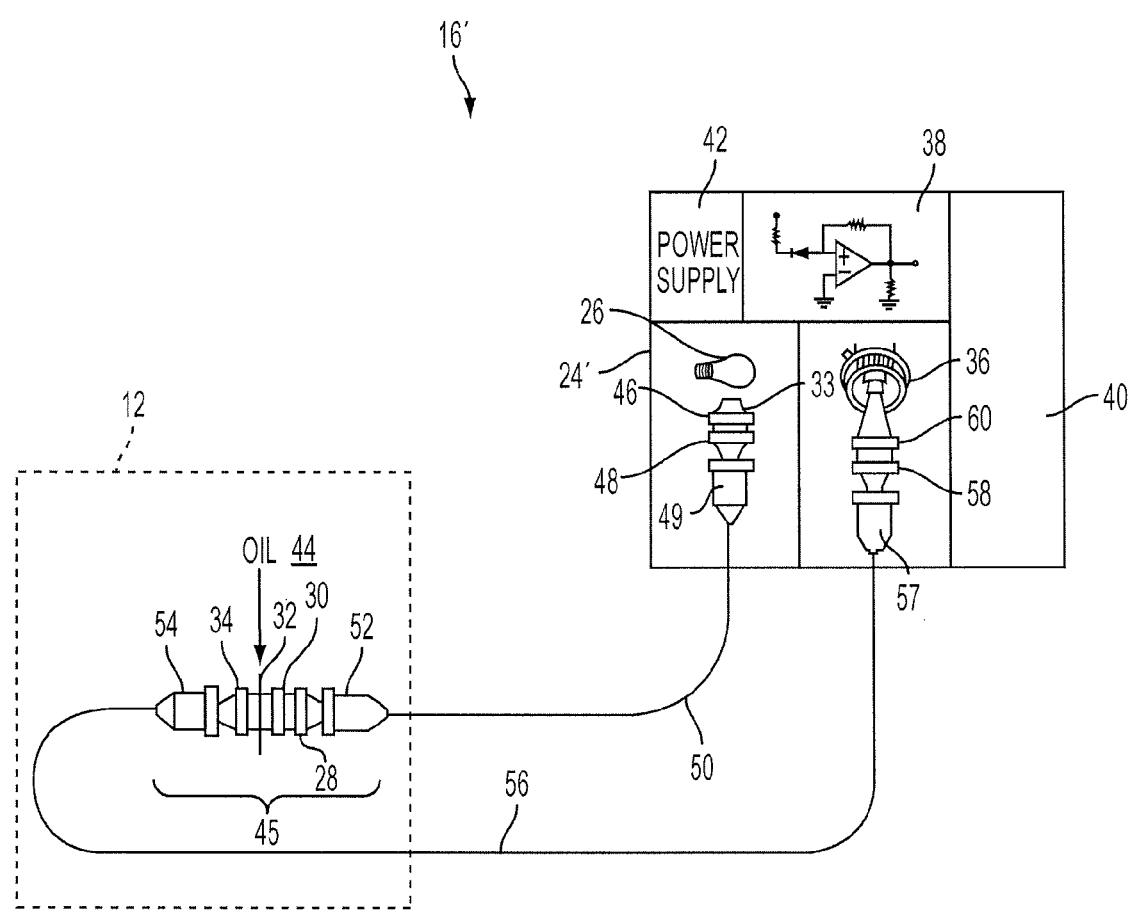
FIG. 3 is an enlarged view of the sensor structure, provided in accordance with another embodiment.

With reference to FIG. 3, a second embodiment of the Furan sensor structure is shown, generally indicated at 16'. The sensor structure 16' is of the invasive type with a sensor head 45 disposed within the tank 12, and with the housing 24' being disposed outside of the tank 12. The housing 24' contains the ultraviolet (UV) light source 26, a collimating lens 46, a condensing lens 48, a fiber optics connector 49 coupled to a first fiber optics cable 50. The other end of the cable 50 has a fiber optics connector 52 within the tank 12 so that the UV light may be transmitted to the window 32 inside of the tank 12. The sensor head 46 also includes the collimating lens 28, the low band (225-330 nm) filter 30, the window 32, and condensing lens 34. Another fiber optics connector 54 is coupled to a second fiber optics cable 56. The other end of the cable 56 includes a fiber optics connector 57 so that UV light passing through the window 32 can be transmitted back to the housing 24' to be received by the light detector 36. A collimating lens 58 and a condensing lens 60 are provided in front of the UV light detector 36 within the housing 24'.

The operational amplifier (OPAMP) 38 amplifies the output of the light detector 36. As in the embodiment of FIG. 2, the output of the OPAMP 38 of FIG. 3 is an electrical signal substantially proportional to the total Furans, mainly the most common element 2FAL=2 Furfuraldehyde. The output of the OPAMP 38 is displayed on a digital display 40. The display 40 or an audible signal can indicate an alarm condition. A universal power supply 42, preferably disposed within the housing 24', provides power to the sensor structure 16'. In either embodiment, the UV light source 26 can be a light emitting diode or a laser.

The sensor head 45 can be incorporated into a tube or probe that can be inserted, in a sealed manner, into the drain valve opening in the tank 12 or any other process pipe of the tank 12 so as to be exposed to transformer oil in the tank 12.

In accordance with the embodiment of FIG. 3, in order to monitor the level of Furans in the oil in the tank 12, oil 44 in the tank 12 surrounds the optical (e.g., glass) window 32. The UV light source 26 emits UV light that passes through the fiber optics cable 50, through lens 28 and filter 30 and through the glass window 32. The fiber optics cable 56 receives the UV light at connector 54, with the photo detector 26 receiving the UV light within the housing 24'. As in the first embodiment of FIG. 2, if Furans are within the oil, the Furans will absorb UV light, thus creating a difference in UV light received by the photo light 36 when compared to the UV light received by the light detector 36 when the oil has no Furans therein. The level of Furnas can be displayed on display 40 of FIG. 3.

Furans, although very important to assess Kraft paper aging in power transformers, are difficult to quantitatively correlate to the actual aging of the solid insulation. Several studies have been carried out in many parts of the world trying to find a good ad universal correlation between Furans and the actual status of the solid insulation. However, such a correlation has yet to be achieved. Researcher and transformer experts agree, however, that the change in Furans level may bring better information than the level itself. Significant changes in the level of Furans may be related to accelerated aging of the transformer or initiation of some faulty condition, particularly due to thermal aspects, but also due to chemical aspects to the insulation, as from, $O_2$, acids and moisture. Thus, using the sensor structure 16, 16' to monitor the change in Furan level online may give transformer users a better insight into what is actually occurring with the insulation.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. An assembly for online monitoring of levels of Furans in oil of a transformer tank, the assembly comprising:
   sensor structure comprising:
      an ultraviolet (UV) light source,
      a filter permitting only UV light of a certain wavelength range to pass the filter,
      a transparent window constructed and arranged so that the filtered UV light passes there-through, and
      a UV light detector constructed and arranged to receive UV light that passes through the window, and
   a transformer tank containing the oil,
   wherein the sensor structure is mounted with respect to a transformer tank that is online so that the window is exposed to oil from the tank that flows past the window, and when Furans in the oil are being monitored, the Furans will absorb UV light, thus creating a difference in UV light received by the light detector when compared to the UV light received by the light detector when the monitored oil has no Furans therein, and
   wherein the light detector is constructed and arranged to provide an output signal that is substantially proportional to a total of Furans in the monitored oil.

2. The assembly of claim 1, wherein the filter is constructed and arranged to filter UV light to a range of 225 to 330 nm.

3. The assembly of claim 1, wherein the light source is a laser.

4. The assembly of claim 1, wherein the light source is a light emitting diode.

5. The assembly of claim 1, wherein the output signal is proportional to 2 Furfuraldehyde and total Furans.

6. The assembly of claim 1, further comprising a collimating lens between the light source and the filter and a condensing lens between the filter and the light detector.

7. The assembly of claim 6, further comprising an amplifier constructed and arranged to amplify the output signal from the light detector.

8. The assembly of claim 7, further comprising a power supply to power the sensor structure, and a digital display to display a level of Furans monitored.

9. The assembly of claim 8, wherein the power supply, the amplifier, the display, the light detector, the lenses, the filter, the window and the light source are all disposed in a single housing.

10. The assembly of claim 9, wherein the tank has a drain valve, the housing having an inlet and an outlet, with the window disposed there-between, the inlet being coupled to the drain valve to receive oil from the tank that passes the window, the outlet being coupled to the tank to return oil to the tank.

11. The assembly of claim 1, wherein the filter and the window are part of a sensor head, the sensor head further comprising a collimating lens between the light source and the filter and a condensing lens between the filter and the light detector, the sensor head being provided inside the tank with the light source and light detector being outside of the tank.

12. The assembly of claim 11, further comprising a first fiber optics cable extending between the collimating lens and the light source and a second fiber optics cable extending between the condensing lens and the light detector.

13. The assembly of claim 12, further comprising a collimating lens and a condensing lens between the light source and the first fiber optics cable, and a collimating lens and a condensing lens between the second fiber optics cable and the light detector.

14. The assembly of claim 13, further comprising an amplifier constructed and arranged to amplify the output signal from the light detector.

15. The assembly of claim 14, further comprising a power supply to power the sensor structure, and a digital display to display a level of Furans monitored.

16. The assembly of claim 14, wherein the power supply, the amplifier, the display, the light detector and the light source are all disposed in a single housing separate from the sensor head.

17. The assembly of claim 16, in combination with the transformer tank with the sensor head being disposed inside the tank so that the window is exposed to oil and the single housing is disposed outside of the tank, with the first fiber optics cable transmitting the UV light to the window and the second fiber optics cable transmitting the UV light, which passes through the window, to the light detector.

18. A method of for online monitoring of levels of Furans in oil of a transformer tank, the method comprising the steps of:
   providing a transformer tank containing oil,
   providing a source of UV light,
   filtering the UV light to a certain wavelength range,
   providing a transparent window that is exposed to the oil of the transformer tank,
   passing the filtered UV light through the window while the transformer is online and while oil flows past the window, and
   receiving the UV light that passes through the window at a light detector, with an output signal of the light detector being substantially proportional to a total of Furans in the oil being monitored.

19. The method of claim 18, wherein the filtering step includes filtering the UV light to a range of 225 to 330 nm.

20. The method of claim 18, wherein the output signal is proportional to 2 Furfuraldehyde and total Furans.

* * * * *